(12) United States Patent
Liu et al.

(10) Patent No.: US 9,814,239 B2
(45) Date of Patent: Nov. 14, 2017

(54) ANTIMICROBIAL COMPLEXES

(75) Inventors: Huiwen Liu, Brighton, MA (US); Boke Zhang, Brighton, MA (US)

(73) Assignees: Huiwen Liu, Brighton, MA (US); Boke Zhang, Brighton, MA (US)

( * ) Notice: Subject to any disclaimer, the term of this patent is extended or adjusted under 35 U.S.C. 154(b) by 1228 days.

(21) Appl. No.: 13/702,623

(22) PCT Filed: Jun. 16, 2011

(86) PCT No.: PCT/US2011/040618
§ 371 (c)(1),
(2), (4) Date: May 22, 2013

(87) PCT Pub. No.: WO2012/012049
PCT Pub. Date: Jan. 26, 2012

(65) Prior Publication Data
US 2016/0073636 A1    Mar. 17, 2016

Related U.S. Application Data (60) Provisional application No. 61/360,182, filed on Jun. 30, 2010.

(51) Int. Cl.
| | | |
|---|---|---|
| *A01N 47/44* | (2006.01) | |
| *D21H 17/07* | (2006.01) | |
| *C09J 11/06* | (2006.01) | |
| *D21H 21/36* | (2006.01) | |
| *C09D 5/14* | (2006.01) | |
| *C08K 5/00* | (2006.01) | |

(52) U.S. Cl.
CPC ............ *A01N 47/44* (2013.01); *C08K 5/0058* (2013.01); *C09D 5/14* (2013.01); *C09J 11/06* (2013.01); *D21H 17/07* (2013.01); *D21H 21/36* (2013.01)

(58) Field of Classification Search
CPC ........ A01N 47/44; C07D 5/14; C08K 5/0058; C09J 11/06; D21H 21/36; D21H 17/07
USPC ........................................................ 514/635
See application file for complete search history.

(56) References Cited

U.S. PATENT DOCUMENTS

2004/0071653 A1*  4/2004  Bratescu ................ A01N 33/12
                                                                424/70.24

* cited by examiner

*Primary Examiner* — Kristin Vajda
(74) *Attorney, Agent, or Firm* — Anova Law Group, PLLC (57) ABSTRACT

The invention generally relates to certain antimicrobial, antibacterial, antifungal or antiviral compounds. More particularly, the invention relates to certain antimicrobial antibacterial, antifungal and/or antiviral compounds, their syntheses and compositions, and methods of use thereof.

49 Claims, 4 Drawing Sheets

ANTIMICROBIAL COMPLEXES

TECHNICAL FIELDS OF THE INVENTION

The invention generally relates to certain antimicrobial, antibacterial, antifungal or antiviral compounds. More particularly, the invention relates to certain antimicrobial antibacterial, antifungal and/or antiviral compounds, their syntheses and compositions, and methods of use thereof.

BACKGROUND OF THE INVENTION

An antimicrobial is a substance that kills or inhibits the growth of microorganisms such as bacteria, fungi, or protozoans. A variety of chemical compounds, natural or synthetic, have been used as antimicrobials. Antimicrobial drugs either kill microbes (microbicidal) or prevent the growth of microbes (microbistatic). For example, disinfectants are antimicrobial substances used on non-living objects. Antimicrobial agents have also been used to control the growth of microorganisms in a variety of industrial processes. Hospital disinfectants, medical device materials may include antimicrobials to prevent infection of patients. Antimicrobials are found in commercial settings, particularly to disinfect contaminated surfaces, as well as in a variety of industrial or household products such as foods, cosmetics, furniture, paints, paper, oil, textile and wood products.

Mixtures of antimicrobial agents have been used for certain applications. For example, a combination of agents may provide antimicrobial effects against a broader spectrum of microbes than a single agent can. A broad spectrum coverage is especially useful in applications where multiple and diverse microorganisms are often encountered. Also, a combination of antimicrobials can make the agents more effective when the antimicrobial composition is to be used for an extended course of treatment. The targeted microbes will have more difficulties to adapt to multiple active ingredients. Moreover, complexes of agents have also been attempted, which have different, yet complementary, physiochemical properties (e.g., U.S. Pat. Nos. 5,629,263 and 3,639,632), although only cationic antimicrobials are generally used together (e.g., U.S. Pat. No. 5,891,921). The anionic, cationic and non-ionic antimicrobial agents are rarely used together due to the potential antagonistic effects.

Despite many antimicrobials are commercially available, problems with effectiveness, sustainability, bioavailability, safety, environmental acceptability, and/or cost remain. Antimicrobials that are ideal for particular applications continue to be sought after. Microorganisms are becoming resistant to current antimicrobial agents. For example, bacteria found in hospital settings are becoming especially drug resistant. There are significant unmet needs for new and improved antimicrobial compounds, compositions, and methods of using the same, particularly compounds that are antiseptic, antifungal, bacteriocidal, bacteriostatic and algae-proofing.

SUMMARY OF THE INVENTION

The invention is based, in part, on the discovery of certain antimicrobial, antibacterial, antifungal or antiviral compounds, their syntheses and composition, and methods of using the same. The present invention combines cation biocide moiety $C^{n+}$ with anion biocide moiety $X^{n-}$ and forms a new entity $C^{n+}X^{-}$. This invention addresses the shortcomings of the previous agents in that the compounds of the invention have broader activity, decreased molar effective concentration, different physical properties from water soluble to water insoluble, good organic solubility, easiness to form film or coating on solid surface, etc.

In one aspect, the invention generally relates to a composition having an anti-microbial, anti-fungal, or anti-viral property comprising an anti-microbial, anti-fungal, or anti-viral effective amount of a compound of Formula I:

(I)

wherein $R_1$ and $R_2$ is independently wherein X is a halogen;
Y is wherein m is an integer from about 1 to about 10;
$X_1, X_2 \ldots X_{n+1}$ is independently an anionic group selected from:

hydroxy, tetraborate

$Na_2B_8O_{13}$, $CH_3(CH_2)_{16}COOH$ (stearate acid), amino acid, acidic peptide, organic phosphic acid, wherein $R_3$, $R_4$ and $R_5$ is independently halogen or $C_1$-$C_6$ alkyl, $R_6$ and $R_7$ is independently $C_1$-$C_6$ alkyl; and n is an integer from about 1 to 20.

In another aspect, the invention generally relates to a method for preventing or reducing microbial, fungal or viral infection. The method includes treating an article in need thereof a solution comprising an anti-microbial, anti-fungal, or anti-viral effective amount of a compound of Formula I:

wherein $R_1$ and $R_2$ is independently wherein X is a halogen;
Y is wherein m is an integer from about 1 to about 10;
$X_1, X_2 \ldots X_{n+1}$ is independently an anionic group selected from:

hydroxy, tetraborate $Na_2B_8O_{13}$, $CH_3(CH_2)_{16}COOH$ (stearate acid), amino acid, acidic peptide, organic phosphic acid, wherein $R_3$, $R_4$ and $R_5$ is independently halogen or $C_1$-$C_6$ alkyl, $R_6$ and $R_7$ is independently $C_1$-$C_6$ alkyl; and n is an integer from about 1 to 20.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties.

As used herein, ($C_x$-$C_y$) refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. ($C_1$-$C_{20}$) and the likes similarly encompass the various combinations between 1 and 20 (inclusive) carbon atoms, such as ($C_1$-$C_6$), ($C_1$-$C_{12}$) and ($C_3$-$C_{12}$).

As used herein, the term "($C_x$-$C_y$)alkyl" refers to a saturated linear or branched free radical consisting essentially of x to y carbon atoms, wherein x is an integer from 1 to about 10 and y is an integer from about 2 to about 20. Exemplary ($C_x$-$C_y$)alkyl groups include "($C_1$-$C_{20}$)alkyl," which refers to a saturated linear or branched free radical consisting essentially of 1 to 20 carbon atoms and a corresponding number of hydrogen atoms. Exemplary ($C_1$-$C_{20}$)alkyl groups include methyl, ethyl, n-propyl, isopropyl, n-butyl, isobutyl, dodecanyl, etc. Of course, other ($C_1$-$C_{20}$)alkyl groups will be readily apparent to those of skill in the art given the benefit of the present disclosure.

As used herein, the term "halogen" refers to fluorine, chlorine, bromine, or iodine.

As used herein, the term "amino" refers to a free radical having a nitrogen atom (i) covalently bonded to two hydrogen atoms, or alternatively (ii) covalently bonded to one hydrogen atom and one carbon radical. As such, the term amino generally refers to primary and secondary amines. In embodiments where the free radical is covalently bonded to a carbon atom, the term "amino" also includes tertiary amines. Those of skill in the art given the benefit of the present disclosure will readily be able to identify when the term "amino" is interchangeably used to refer to primary, secondary, and tertiary amines.

BRIEF DESCRIPTION OF THE DRAWINGS

The figures presented here are a series of rigorous fluorescent imaging analysis experiments to discover a working model for yeast viability measurement directly from fermenters, where the fluorescent reagents are not in the normal range of the optimized conditions.

DETAILED DESCRIPTION OF THE INVENTION

Figure 1:
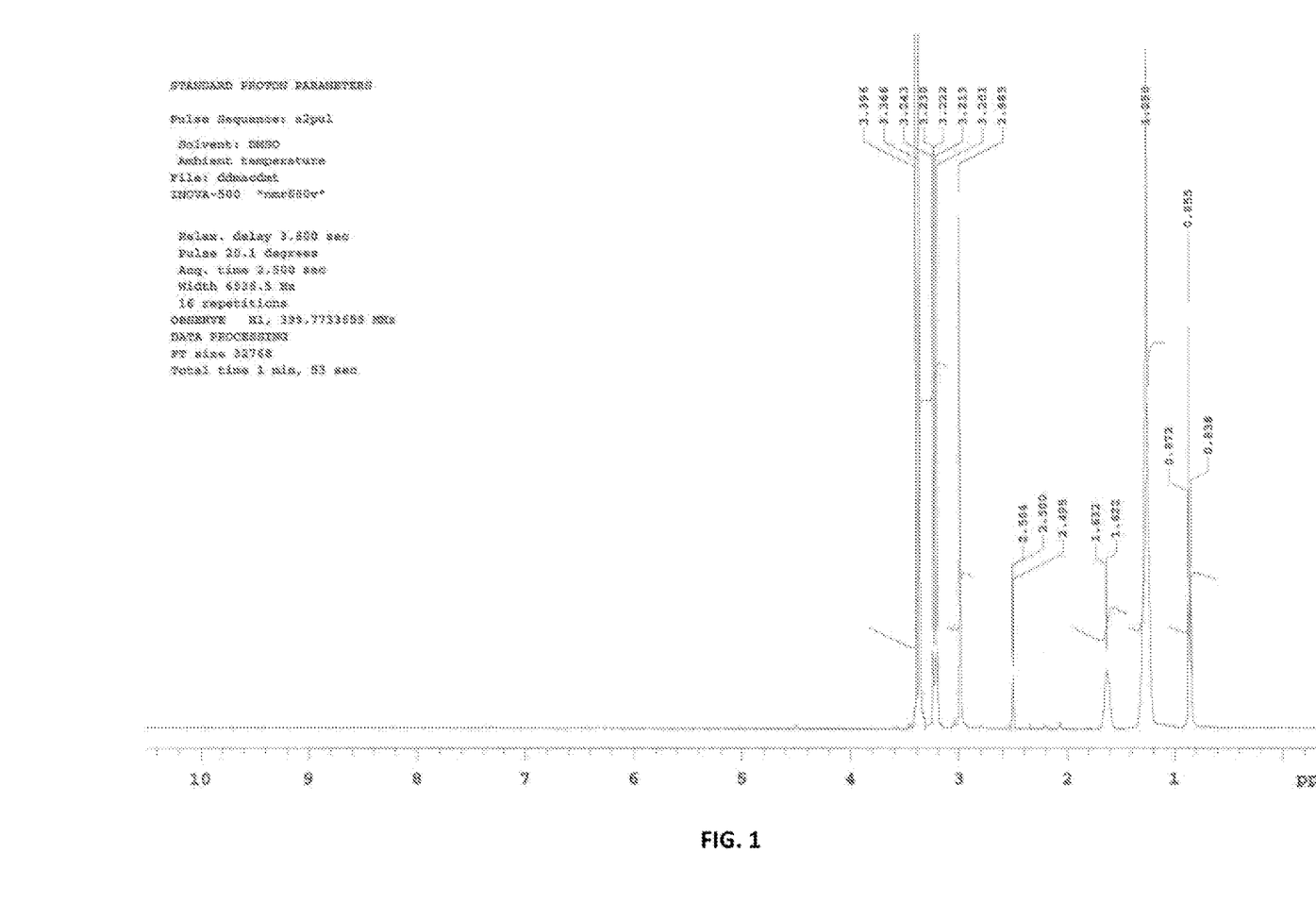
FIG. 1 depicts a proton NMR Spectrum of DDMAC-DMT (Example 4).
Figure 2:
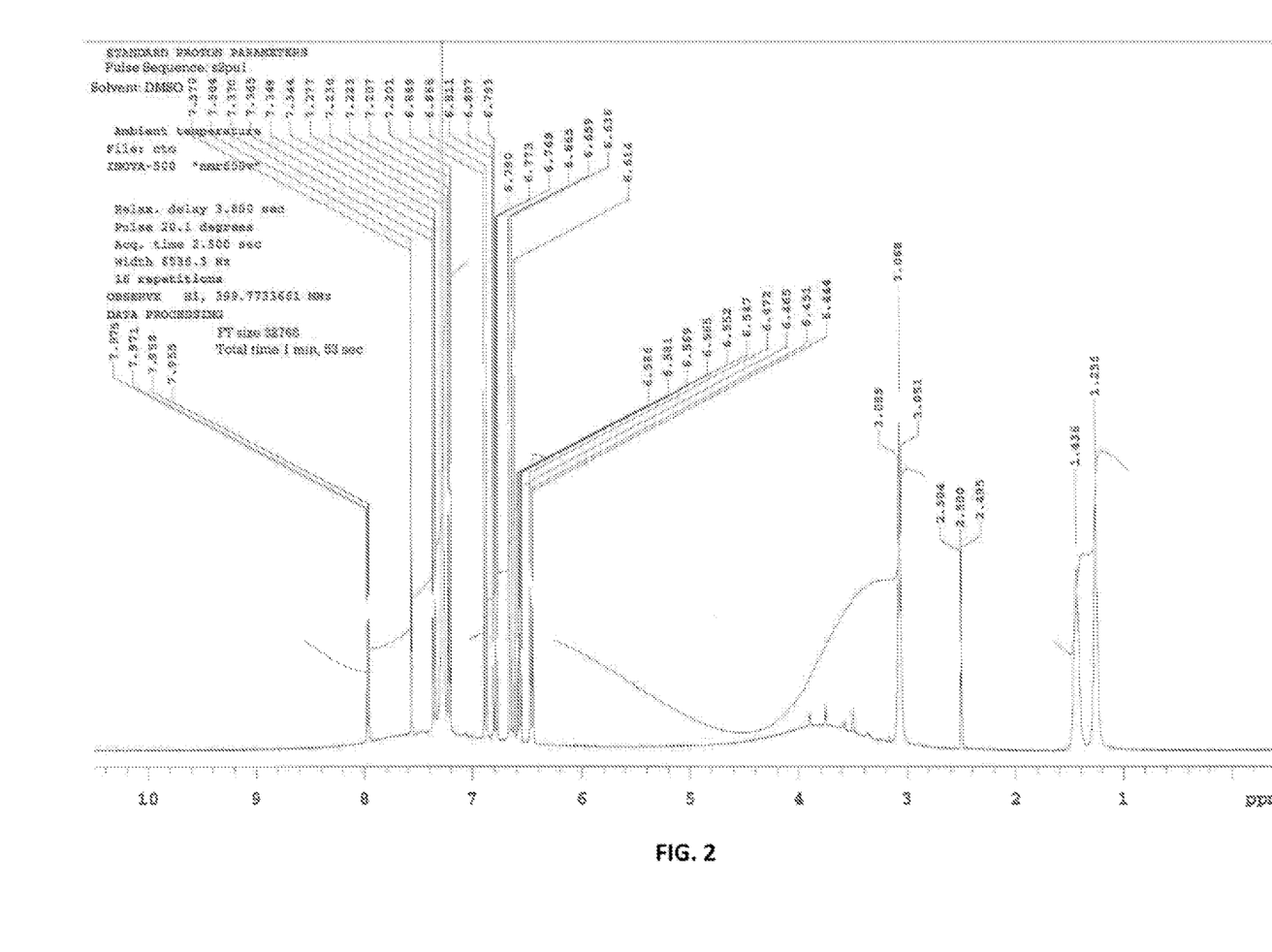
FIG. 2 depicts a proton NMR Spectrum of Chlorohexidineomidinetriclosan (Example 5).
Figure 3:
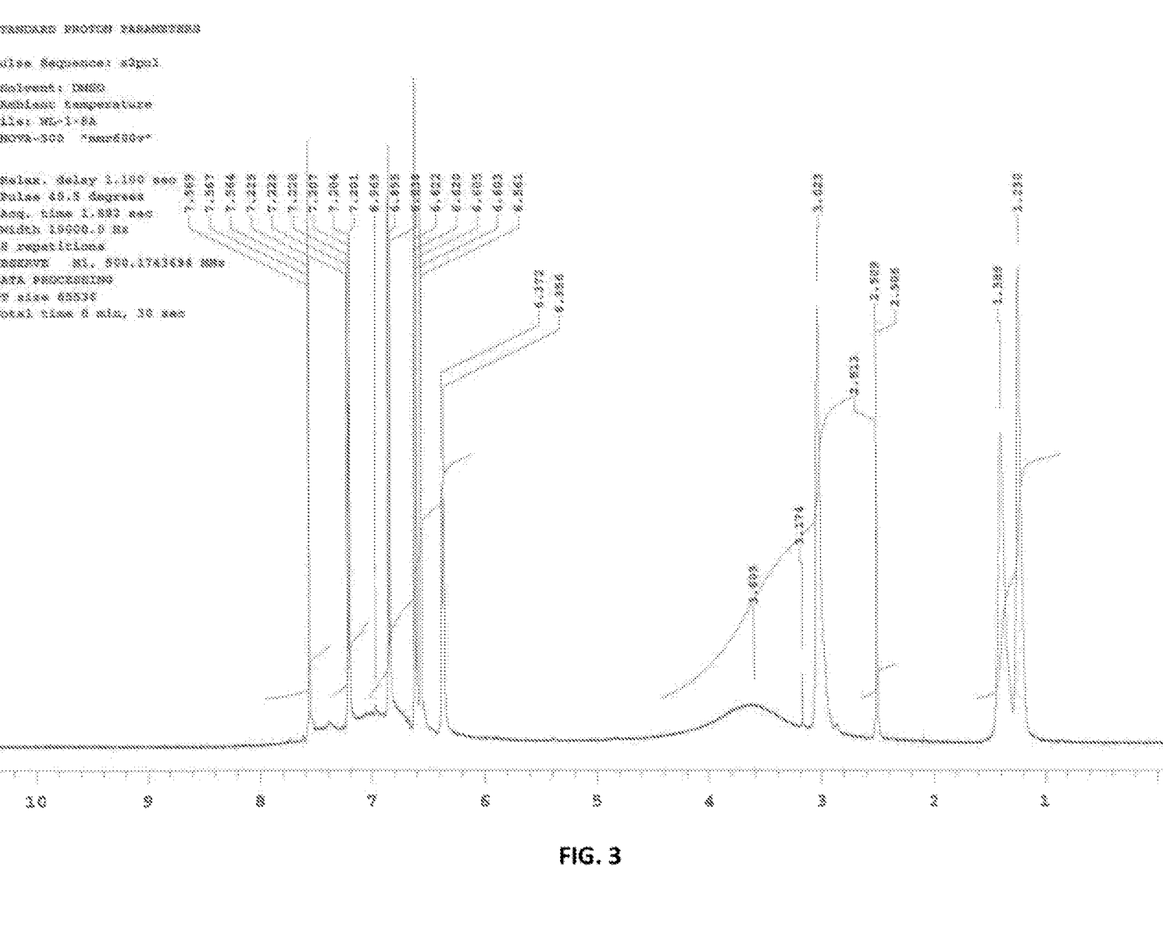
FIG. 3 depicts a proton NMR Spectrum of PHMB.Tc (Example 6).
Figure 4:
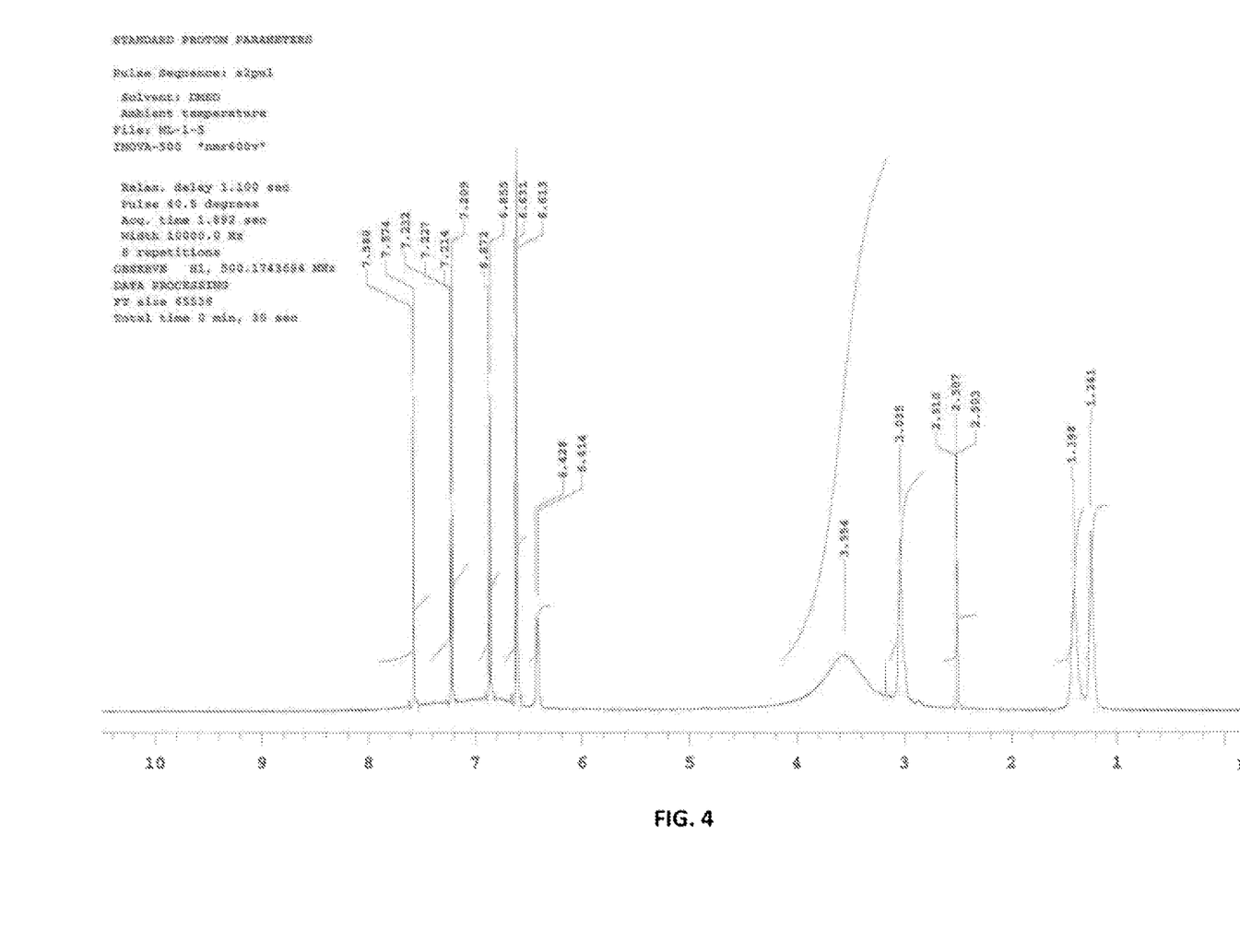
FIG. 4 depicts a proton NMR Spectrum of Chlorohexidinetriclosan (Example 7).

The present invention relates to compounds, compositions, methods for making and using the same. The synthetic antimicrobial compounds (organic salts) that possess antibacterial, antimicrobial, antifungal and antiviral properties represent significant improvement over the currently available agents.

The new compounds are complexes prepared from cationic and ionic biocides. The structures of these novel complexes formed were characterized by NMR spectrometer. The NMR spectra of the complex are differed from the cationic, anionic or non-anionic component.

In one aspect, the invention generally relates to a composition having an anti-microbial, anti-fungal, or anti-viral property comprising an anti-microbial, anti-fungal, or anti-viral effective amount of a compound of Formula I:

wherein $R_1$ and $R_2$ is independently wherein X is a halogen;
Y is wherein m is an integer from about 1 to about 10;
$X_1$, $X_2$ ... $X_{n+1}$ is independently an anionic group selected from:

hydroxy, tetraborate

$Na_2B_8O_{13}$, $CH_3(CH_2)_{16}COOH$ (stearate acid), amino acid, acidic peptide, organic phosphic acid,
wherein $R_3$, $R_4$ and $R_5$ is independently halogen or $C_1$-$C_6$ alkyl, $R_6$ and $R_7$ is independently $C_1$-$C_6$ alkyl; and n is an integer from about 1 to 20.

In certain embodiments, the preferred n is 1 or 2. In other preferred embodiments, n is an integer from 2 to 10. In some embodiments, m is preferably 3, 4, 5, 6 or 7. In some embodiments, the preferred halogen is Cl.

In some embodiments, $X_1, X_2 \ldots X_{n+1}$ is independently an anionic group selected from:

(II)

(III)

(IV)

In some other embodiments, $X_1, X_2 \ldots X_{n+1}$ is independently an anionic group selected from:

(II)

(III)

In some embodiments, the ratio of (II) to (III) is about 1.

In some embodiments, $X_1, X_2 \ldots X_{n+1}$ is independently an anionic group selected from:

(II)

(IV)

In some embodiments, the ratio of (II) to (IV) is about 1.

In some embodiments, $X_1, X_2 \ldots X_{n+1}$ is independently an anionic group selected from:

(III)

(IV)

In some embodiments, the ratio of (III) to (IV) is about 1.

In another aspect, the invention generally relates to a method for preventing or reducing microbial, fungal or viral infection. The method includes treating an article in need thereof a solution comprising an anti-microbial, anti-fungal, or anti-viral effective amount of a compound of Formula I:

wherein $R_1$ and $R_2$ is independently wherein X is a halogen;
Y is wherein m is an integer from about 1 to about 10;
$X_1, X_2 \ldots X_{n+1}$ is independently an anionic group selected from:

hydroxy, tetraborate $Na_2B_8O_{13}$, $CH_3(CH_2)_{16}COOH$ (stearate acid), amino acid, acidic peptide, organic phosphic acid, wherein $R_3$, $R_4$ and $R_5$ is independently halogen or $C_1$-$C_6$ alkyl, $R_6$ and $R_7$ is independently $C_1$-$C_6$ alkyl; and n is an integer from about 1 to 20.

The cation and anion biocides may be selected to target different organisms. For example, cationic biocide PHMB (Vantocil 100) possess activity against gram positive and gram negative bacteria, while anionic biocide sodium omadine are useful against fungus (see following table for a summary). The complex of PHMB and omadine provides different and complementary the bioactivities, thereby increasing the utility scope as well as the antimicrobial bioactivity.

TABLE 1

|  |  |  | Sodium Omadine (ppm) | Vantocil 100 (ppm) |
|---|---|---|---|---|
| Bactericide | Gram Positive | Bacillus subtilis | 0.5 | 1 |
|  |  | Staphylococcus aureus | 16 | <1 |
|  |  | Streptococcus faecalis | 2 | 5 |

TABLE 1-continued

|  |  |  | Sodium Omadine (ppm) | Vantocil 100 (ppm) |
|---|---|---|---|---|
|  | Gram Negative | Escherichia coli | 16 | 1 |
|  |  | Proteus vulgaris | 8 | 40 |
|  |  | Pseudomonas aeruginosa | 128 | 20 |
|  |  | Salmonella typhimurium | 16 | 2 |
| Fungicide | Molds | Aspergillus niger | <0.25 | 150 |
|  | Yeasts | Endomycopsis albicans | <0.25 | 60 |
|  | Amoeba | Saccharomyces cerevisiae | <0.25 | 20 |

Vantocil 100 is a 95% strength solid form of a broad spectrum, fast acting bactericide poly(hexamethylene biguanide)hydrochloride (PHMB). PHMB is used in the formation of disinfectants and sanitizers for use in industrial, institutional, agricultural, food, beverage and domestic products and applications.

In some embodiments, the invention is related to the antimicrobial complexes synthesized from amines (e.g., primary, secondary, tertiary or quaternary amines) with phenolic compounds such as triclosan (Structure A), with mercapto or thio (—SH) compounds such as omadine (Structure B), or with dimethyldithiocarbamate (Structure C).

The complexes may also be synthesized from chlorohexidine and its salt with both phenolic compounds such as triclosan and mercapto and thio compounds, such as omadine or dimethyldithiocarbamate (Structures D and E). The amine triclosan complexes and amine omadine complexes have general chemical structures as shown below in Structures A, B and C, respectively.

Structure A

Structure B

Structure C

Structure D

-continued

Structure E

The primary, secondary, tertiary and quaternary amines have following general structure as salt form (cationic):

Typical example of the amines is didecyldimethylammonium as shown below, which is commercially available as biocide and is formulated in the chloride form, and marketed as Bardac by Lonza Inc under the trademark Bardac 2250 and 2280.

Triclosan is a phenolic biocide and has the following structure.

Omadine is an organic mercapto compound and can form an anionic salt form easily in the presence of a base, such as NaOH. Omadine and its sodium salt form have the following structures.

Omadine    Omadine Sodium Salt

Dimethyldithiocarbamate is an organic thio compound and can form the anionic salt form easily in the presence of a base, such as NaOH. Dimethyldithiocarbamate and its sodium salt form have the following structures.

Dimethyldithiocarbamate    Dimethyldithiocarbamate
(R5 = R6 = Methyl)    Sodium Salt
(R5 = R6 = Methyl)

Preparation of the New Compounds (Complexes)
Method 1

Dissolve triclosan in organic solvent, preferably methanol or ethanol. Slowly pour the solution to the reactant polybiguanide solution. Leave the reaction mixture stirring over night. One equivalent of NaOH may be necessary to add to the mixture during the reaction. The by-product Na salt can be removed by filtration at end of reaction. The organic solvent is then removed under vacuum. The solid complexes after vacuum can be used as is, or further purified by known procedures such as recrystallization.

Method 2

Phenols are weak acids that can dissociate in solution to give H+ plus a phenoxide anion, ArO—. It can also react with strong base to form the anionic ion. For example, triclosan reacts with 1 equivalent sodium hydroxide in water solution to form triclosan sodium salt which is a clear solution. Slowly pour this phenolic solution to the reactant polybiguanide aqueous solution. Leave the reaction mixture stirring until the reaction is finished as is indicated by the precipitation of the formed complexes from solution. The solid complexes is filtered and washed with water. The crude product can be used as is, or further purified by known procedures such as recrystallization.

Amine Salt

The formed base reacted with polybiguanide and give polybiguanide triclosan complexes.

Method 3

The complexes can also be prepared during the process of the product material on purpose. For example, add both polybiguanide and triclosan into the product manufacturing process in various amounts to achieve the formation of the complexes in-situ for desired bioactivities.

Method 4A Preparation of Organic Amine-Triclosan (Phenolic) Compounds (Complexes)

Dissolve triclosan in organic solvent, preferably methanol or ethanol. Slowly pour the solution to the reactant organic amine compound (salts) solution. Leave the reaction mixture stirring over night. One equivalent of NaOH may be necessary to add to the mixture during the reaction. The by-product Na salt can be removed by filtration at end of reaction. The organic solvent is then removed under vacuum. The solid complexes after vacuum can be used as is, or further purified by known procedures, such as recrystallization.

Method 4B Preparation of Organic Amine-Triclosan Complexes (Salts)

Phenols are weak acids that can dissociate in solution to give $H^-$ plus a phenoxide anion, $ArO^{31}$. It can also react with strong base to form the anionic ion. For example, triclosan reacts with 1 equivalent sodium hydroxide in water solution to form triclosan sodium salt, which is a clear solution. Slowly pour this basic phenolic solution to the reactant organic amine salt aqueous solution. Leave the reaction mixture stirring until the reaction is finished as is indicated by the precipitation (or phase separation) of the formed complexes from solution. The solid complexes is filtered (or separated) and washed with water (some compound has high water solubility and this step can be modified or eliminated). The crude product can be used as is, or further purified by known procedures such as recrystallization.

The formed base (triclosan sodium salt) then reacted with the organic amine salts such as didecyldimethylammonium chloride or Bardarc and gave the desired amine triclosan complex.

Omadine Sodium Salt

New Compounds (Complexes B)

Method 5A Preparation of Organic Amine-Omadine Compounds (Complexes)

Dissolve sodium omadine in water or use commercial sodium omadine solution (40% in water). The reactant organic amine salt (neat or use the commercial aqueous solution, Bardac 2250 is a 50% aqueous solution of didecyldimethylammonium chloride) is added to the omadine aqueous solution. Leave the reaction mixture stirring over night. The aqueous is separated from the product. The crude product (didecyldimethyl ammonium omadine is a brown oil on top layer) is separated, washed with saturated NaCl solution. The brown color can be removed by active charcoal.

Method 5B Preparation of Organic Amine (Didecyldimethylammonium)-Omadine Compounds (Complexes)

Use omadine itself or use HCl to convert omadine sodium salt to free omadine form. For the latter, dissolve omadine sodium salt in HCl aqueous solution for conversion. Extract the omadine with organic solvent toluene from the aqueous solution after conversion. The organic layer is washed with water and saturated NaCl solution, and dried with sodium sulfate. The organic solvent was removed under vacuum and the free omadine is obtained. Then dissolve free omadine in methanol or ethanol. Slowly pour this omadine solution to the reactant organic amine salt (didecyldimethylammonium chloride or Bardac) solution. One equivalent of NaOH may be necessary to be added to drive the reaction to completion. Leave the reaction mixture stirring over night until the reaction is finished as is indicated by the precipitation or separation of the formed compounds (complexes) from solution. The compound is separated and washed. The crude product can be used as is, or further purified by known procedures such as discolorations or recrystallization.

Method 6 Preparation of Organic Amine-Triclosan and Amine-Omadine Compounds (Complexes) and Chlorohexidine-Triclosan-Omadine/Dimethyldithiocarbamate Derivatives

These new amine mercapto complexes can also be prepared during the process of the product material on purpose. For example, add both organic amine salts and omadine or its salt form into the product manufacturing process to achieve the formation of the complexes in-situ for desired bioactivities. Likewise the amine phenolic complexes can also be prepared by adding both the organic amine salts and triclosan or its salt form into the product manufacturing process in various amounts to achieve the formation of the complexes in-situ for desired bioactivities. Similarly the new complexes (compounds) from chlorohexidine and phenolic compounds, from chlorohexidine and mercapto (thio) compounds, from chlorohexidine with both phenolic compounds such as triclosan and thio compounds such as omadine or dimethyldithiocarbamate can also be generated in-situ for desired bioactivities in this way.

Method 7 Preparation of Organic Amine-Dimethyldithiocarbamate Compounds

Dissolve sodium dimethyldithiocarbamate in water or use commercial sodium dimethyldithiocarbamate solution (40% in water). The reactant organic amine salt (neat or use the commercial aqueous solution) is added to sodium dimethyldithiocarbamate solution. Leave the reaction mixture stirring over night. The aqueous is separated from the product. The crude product (didecyldimethyl ammonium dimethyldithiocarbamate is a light yellow solid) is filtered and washed with water.

Method 8 Preparation of Chlorohexidine-Triclosan-Omadine Compound

Use commercial available chlorohexidine salt (for example chlorohexidine digluconate 20% solution) (1 equivalent). Triclosan (1 equivalent) reacts with 1 equivalent sodium hydroxide in water solution to form triclosan sodium salt, which is a clear solution. Slowly pour this basic phenolic solution to the reactant chlorohexidine aqueous solution. Leave the reaction mixture stirring until the reaction is finished as is indicated by the precipitation of the formed compound from solution. Sodium omadine (1 equivalent), 40% aqueous solution is added to the above reaction mixture. The reaction mixture is stirred and mixed well and stand overnight (dilution with water may be needed). The white (off-white) solid product is filtered and washed with water. This new compound can also be prepared by mixing 1 equivalent each of chlorohexidine, triclosan and omadine in solution and stirring over night (heat may be needed for the reaction).

MD168

MD 169 (chlorohexidine-triclosan-dimethyldithiocarbamate compound) and MD 170 (chlorohexidine-omadine-dimethyldithiocarbamate compound), MD 171 (chlorohexidine-triclosan-triclosan compound) and MD 172 (chlorohexidine-dimethyldithiocarbamate-dimethyldithiocarbamate compound) can be prepared in the similar manner as above. Their chemical structures are shown below.

MD 169

(chlorohexidine-triclosan-dimethyldithyldithiocarbamate compound)

MD 170

(chlorohexidine-omadine-dimethyldithyldithiocarbamate compound)

MD 171

(chlorohexidine-triclosan-triclosan compound)

MD 172

(chlorohexidine-dimethyldithyldithiocarbamate-dimethyldithyldithiocarbamate compound)

The present invention relates generally to a synthesis and preparation of antimicrobial (antibacterial, antifungal and antiviral) compounds (complexes) prepared from Primary, Secondary, Tertiary and Quaternary Amines with Phenolic (such as Triclosan) or Mercapto (thiol compound such as Omadine) derivatives; prepared from chlorohexidine and Phenolic (such as Triclosan) or Mercapto (such as Omadine) or Thio compounds (such as dimethyldithiocarbamate). The new compounds also include the "cross-mixed" products prepared from chlorohexidine with Phenolic (such as Triclosan) and Mercapto (such as Omadine) and Thio compounds (such as dimethyldithiocarbamate). The synthesized compounds have new physical properties, broader and synergistic bioactivities against fungi, bacteria, and viral microbes.

Optional Adjunct Ingredients

The compositions of the invention may include one or more adjunct ingredients, for example to facilitate formulation of a composition, to modify a composition to achieve a desired mildness, to boost particular antimicrobial effectiveness, to improve wetting characteristics for a target substrate, to enhance aesthetic characteristics of the product, etc. The compositions of the invention may include, for example, an alcohol solvent. Exemplary alcohol solvents include ethanol, propanol, butanol, propylene glycol, diethylene glycol, dipropylene glycol and mixtures thereof.

In some application, it is desirable to include emulsifiers, such alkyl polyether-type emulsifiers, to enhance physical stability of the antimicrobial product. Examples of alkyl polyether-type emulsifiers suitable for incorporation into the antimicrobial compositions disclosed herein include: isoceteth-20 (CAS No. 69364-63-2) and ceteth-20 (CAS No. 9004-95-9).

For certain applications of disinfectants, surfactants are preferably used. Surfactants may help with achieve uniform wetting of the surface to be treated and may have an added cleaning effect.

Other ingredients may be included into an antimicrobial composition to achieve physical stability for certain products, such as perfumes and skin emollients. For example, sulfonate anionic surfactant having a chain length of $C_{12}$ to $C_{18}$ may be useful.

Stabilizing agents, organic or inorganic, may be added to compositions and products of the invention, for example, certain nonionic materials, polymeric materials, electrolytes, and mixtures thereof. Stabilizing agent, or mixture of stabilizing agents, should be added at a level necessary to prevent or retard surfactant precipitation, for example. Electrolytes are water soluble salts having a mono-, di-, or trivalent cation. Examples of electrolytes include chlorides, sulfates, nitrates, carbonates, and mixtures thereof, of sodium, ammonium, magnesium, potassium, and/or aluminum.

The pH of an antimicrobial composition may be important and should be adjusted or buffered to achieve the desired range.

Certain antimicrobial compositions, for examples, surface cleaner products may include some perfume to provide an olfactory aesthetic benefit and to mask an existing odor. Depending on the application and the product, the perfumes to be used may preferably be those that are water-soluble and/or volatile to minimize spotting and filming. Flavoring agents may also be included as to further enhance the aesthetics of a product. Flavoring agents include those typically used in food and include extracts and artificial flavors, e.g., vanilla, fruit flavors, and the likes. Similarly, suitable sweetening agents may be used in the compositions, such as natural and artificial sweeteners such as sucrose, fructose, dextrose, invert sugar, sorbitol, aspartame, saccharin.

Products Incorporating Antimicrobial Compositions

The products containing the antimicrobial compositions of the invention include many diverse categories of products, such as personal care products, household care products, skin care/cosmetic products, wood preserving products, surface cleaning products, etc.

Examples, of personal care products include hand soaps, hand sanitizers, body washes, mouth washes, toothpastes, shower gels, shampoos, body lotions, deodorants, nasal sprays, foot care, vaginal care and/or wash, pet care and combinations thereof. A personal care product may take the form of a wipe product, particularly suitable for wiping or drying the face or hands. The antimicrobial compositions of the invention may be embedded or impregnated into a wipe product. A personal care product herein may also take the form of a tissue, towel, napkin or diaper.

Examples of household care products include hard surface cleaners, deodorizers, fabric care compositions, fabric cleaning compositions, manual dish detergents, automatic dish detergents, floor care compositions, kitchen cleaners or disinfectants, bathroom cleaners or disinfectants and combinations thereof.

Antimicrobial compositions and products of the invention are suitable for a variety of uses. Suitable uses include the eradication of microbes, bacteria and/or viruses. The method of use may include the steps of topically applying a composition and/or product of the invention to an area in need of treatment.

The exact amount of antimicrobial composition and/or nature of a product will depend upon the needs and abilities of the formulator and practitioner of the present methods.

EXAMPLES

Example 1

Preparation of Didecyldimethylammonium-Triclosan Compounds

Triclosan (54.1 g, 0.187 mol) was added in NaOH (7.5 g in 20 ml water, 0.187 mol) solution, heated to 60° C. until a yellow clear solution was formed. This solution was added to the didecyldimethyl ammonium chloride (Bardac, 50%, 135 ml, 0.187 mol) solution, and stirred and heated to 80° C. for 2 hrs. Cool the reaction mixture to room temperature and two phases were formed. Remove the top aqueous phase. The bottom oily phase was washed with saturated sodium chloride solution and dried. Weight: 114 g (100%, yield). 1H NMR (400 MHz, d-DMSO) δ: 7.40 (1H), 7.09(1H), 6.62 (1H), 6.54 (1H), 6.29 (1H), 5.94 (1H), 3.74, 3.14 (4H), 2.91 (6H), 1.93, 1.53 (4H), 1.19(28H), 0.80(6H).

Example 2

Preparation of Cetylpyridinium-Triclosan Compounds

Triclosan (29 g, 0.1 mol) was added in NaOH (5M, 2 ml, 0.1 mol) solution, heated until a yellow clear solution was formed. The cetylpyridinium chloride (white crystal, 0.1 mol) was added to the above solution, stirred for 2 hrs. The solid product formed was filtered and gave semi-solid (orange) product, dried. Weight: 73.7 g (120%, yield with moisture). $^1$H NMR (500 MHz, d-DMSO) δ: 9.10(2H), 8.61

(1H), 8.17(2H), 7.61 (1H), 7.24(1H), 6.92 (1H), 6.76 (1H), 6.64(1H), 6.59 (1H), 3.38 (water), 1.23 (24H), 0.86 (3H).

Example 3

Preparation of Didecyldimethylammonium-Omadine Compounds

Didecyldimethylamonium bromide (81.4 g, 75% gel in water, 0.17 mol) was added to sodium omadine (56 ml, 28.2g, 0.2 mol) solution, mixed well and stirred for 2 hrs. Collect the desired product (top brown oil) and wash it with braine (saturated NaCl solution), dry it. Weight 102.2 g (133% yield containing water, structure is not fully assigned yet with NMR).

Example 4

Preparation of MD 148 (Didecyldimethylammonium-Dimethyldithiocarbamate Compound)

Dimethyldithiocarbamate sodium solution (40% w/w in water, 14.3 g active, 0.1 mol, 35.75 g solution) is added in Bardac 2250 (50% solution, 72.2 ml, 36.1 g active, 0.1 mol). The reaction mixture is mixed well and stirred overnight. The formed light yellow solid is filtered and washed with water. After air-dried, weight: 40 g (90% yield). Molecular formula: $C_{25}H_{54}N_2S_2$. Molecular weight: 446.84. $^1$H NMR (400 MHz, d-DMSO) δ: 3.40 (s, 6H), 3.37 (water), 3.22 (m, 4H), 2.99 (s, 6H), 1.62 (m, 4H), 1.25 (m, 28H), 0.86 (m, 6H).

Example 5

Preparation of MD 168 (Chlorohexidine-Omadine-Triclosan Compound)

Triclosan (MW 289.53, 2.9 g, 0.01 mol) is added to sodium hydroxide solution (MW 40, 0.4 g, water 2 ml). This solution is stirred until a clear solution is obtained. The resultant solution is added to the chlorohexidine digluconate (20% solution in water, MW 896.9, 45 ml, 0.01 mol) slowly. The off-white solid (product) is formed in the solution. To this solution is added following sodium omadine (40% solution, MW 149.15, 1.49 g, around 3.7 g solution, 0.01 mol) and mixed well. Water (20 ml) is added into the mixture and mixed well, then keep it stand overnight. The newly formed off-white solid is then filtered and washed with water, air-dried. Weight: 10.5 g (110%, with moisture or maybe hydrate water form). Molecular formula: $C_{39}H_{42}C_{16}N_{11}O_3S$. Molecular Weight: 922.15. $^1$H NMR (400 MHz, d-DMSO) δ: 7.97(dd, 1H), 7.57(d, 1H), 7.36(dd, 1H), 7.28(bs, 8H), 7.22 (dd, 1H), 6.88 (d, 1H), 6.79 (m, 1H), 6.66(d, 1H), 6.63 (d, 1H), 6.57(dt, 1H), 6.46(dd, 1H), 3.07(t, 4H), 1.44 (bs, 4H), 1.26 (s, 4H).

Example 6

Preparation of PHMB Triclosan Complex (1:1)

Triclosan (14.5 g, 0.05 mol) was added into NaOH solution (2 g in 10 ml water, 0.05 mol), stirred and heated until all dissolved in solution. The resultant solution was added into Vantocil (20% PHMB in water) solution (55 ml) with stirring. Then diluted with water (100 ml), stirred/mixed well and filtered. The white solid was washed with water and air-dried. Weight: 22.3 g (94%, yield). 1H NMR (500 MHz, d-DMSO) δ: 7.58(1H), 7.22(1H), 6.87(1H), 6.63(2H), 6.46(1H), 3.04 (4H), 1.40(4H), 1.24 (4H).

Example 7

Preparation of Chlorohexidine Triclosan Complex (1:1)

Triclosan (5.8 g) was added to sodium hydroxide solution (5M, 4 ml, 0.02 mol), stirred and heated until a light yellow solution obtained. This solution was then added to chlorohexidine digluconate solution (20%, 45 ml), mixed well and stirred. A white precipitate was formed, filtered, washed with water and air-dried. Weight: 11.1 g (102%). 1H NMR (500 MHz, d-DMSO) δ: 7.56(1H), 7.23(4H), 7.21(1H), 7.03(4H), 7.12 (1H), 6.88(1H), 6.64 (1H), 6.44 (1H), 3.08 (4H), 1.45 (4H), 1.28 (4H).

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

We claim:

1. A composition having a formula: $C^{n+}X^{n-}$, wherein:

$C^{n+}$, is a cation and selected from poly(hexamethylene) biguanide, biguanide, Poly(2-hydroxypropyl dimethyl ammonium), polyquaternary ammonium, quaternary ammonium, tertiary ammonium, secondary ammonium, primary ammonium, protonated imine, secondary and quanternary amine polymer, protonated organic guanidine, polyphosphonium, or a combination thereof; and $X^{n-}$, is an anion and selected from phenolate, triclosan, pyrithione (omadine), dithiocarbamate, ethylenebisdithiocarbamate, hydroxyl, borate, carboxylate, fatty acid, amino carboxylate, peptide with carboxylate group, organic phosphate, or a combination thereof; and wherein said $C^{n+}X^{n-}$ is a composition of Formula I:

wherein
R_1 and R_2 is selected from aliphatic, aromatic, nitrile, guanidine or amine group;
Y is wherein m is an integer from about 1 to 20;
$X_1, X_2 \ldots X_{n+1}$ is an anionic group selected from phenolic group, pyrithione group, dithiocarbcarbamate group, hydroxyl group, borate group, carboxylic group, fatty acid, amino acid group, acidic peptide group, organic phosphate, or a combination thereof, wherein $X_1+X_2+\ldots+X_{n+1}=100\%$ and n is an integer from 1 to 100.

2. The composition of claim 1, wherein $C^{n+}$ is poly(hexamethylene) biguanide.

3. The composition of claim 1, wherein $C^{n+}$ is biguanide.

4. The composition of claim 1, wherein $C^{n+}$ is Poly(2-hydroxypropyl dimethyl ammonium).

5. The composition of claim 1, wherein $C^{n+}$ is polyquaternary ammonium.

6. The composition of claim 1, wherein $C^{n+}$ is quaternary ammonium.

7. The composition of claim 1, wherein $C^{n+}$ is tertiary ammonium.

8. The composition of claim 1, wherein $C^{n+}$ is protonated secondary amine.

9. The composition of claim 1, wherein $C^{n+}$ is protonated primary amine.

10. The composition of claim 1, wherein $C^{n+}$ is protonated imine.

11. The composition of claim 1, wherein $C^{n+}$ is secondary and quanternary amine polymer.

12. The composition of claim 1, wherein $C^{n+}$ is guanidine.

13. The composition of claim 1, wherein $x^{n-}$ is $X_1$, $X_2, \ldots X_n$.

14. The composition of claim 1, wherein $X^{n-}0$ is phenolate group.

15. The composition of claim 1, wherein $X^{n-}$ is triclosan.

16. The composition of claim 1, wherein $X^{n-}$ is pyrithione (omadine).

17. The composition of claim 1, wherein $X^{n-}$ is dithiocarbamate.

18. The composition of claim 1, wherein $X^{n-}$ is ethylenebisdithiocarbamate.

19. The composition of claim 1, wherein $X^{n-}$ is hydroxyl.

20. The composition of claim 1, wherein $X^{n-}$ is borate.

21. The composition of claim 1, wherein $X^{n-}$ is carboxylate.

22. The composition of claim 1, wherein $X^{n+}$ is anion of fatty acid.

23. The composition of claim 1, wherein $X^{n-}$ is amino acid anion.

24. The composition of claim 1, wherein $X^{n-}$ is peptide with carboxylate.

25. The composition of claim 1, wherein $X^{n-}$ is organic phosphate.

26. The composition of claim 1, wherein m is an integer from about 1 to 20.

27. A method for preparing the composition having the formula $C^{n+}X^{n-}$ in claim 1, the method comprising:
having an anion biocide solution and one equivalent sodium hydroxide react with each other in water or in an organic solvent;
adding in cation biocide solution slowly and stirring at room temperature or higher temperature to prepare a product solution; and
filtering out and washing a byproduct sodium salt from the product solution.

28. A method for preparing the composition having the formula $C^{n+}X^{n-}$ in claim 1, the method comprising:
mixing an aqueous or organic solvent solution of anion biocide and cation biocide together at room temperature or higher temperature, following by adding one equivalent of sodium hydroxide and stirring at room temperature or higher temperature to prepare a product solution; and
filtering out and washing a byproduct sodium salt from the product solution.

29. A method for preparing the composition having the formula $C^{n+}X^{n-}$ in claim 1, the method comprising:
having anion biocide and cation biocide in contact with each other in an aqueous or organic solvent solution to form the composition of $C^{n+}X^{n-}$.

30. A method, comprising:
treating an article with a solution, a gel, a cream, a lotion, a emulsion or a material containing an effective amount of the composition of $C^{n+}X^{n-}$ of claim 1.

31. The method of claim 30, wherein the method prevents, reduces or heals the microbial infection.

32. The method of claim 30, wherein the method prevents, reduces or heals the bacteria infection.

33. The method of claim 30, wherein the method prevents, reduces or heals the fungal infection.

34. The method of claim 30, wherein the method prevents, reduces or heals the viral infection.

35. The method of claim 30, wherein a solution is used.

36. The method of claim 30, wherein a gel is used.

37. The method of claim 30, wherein a cream is used.

38. The method of claim 30, wherein a lotion is used.

39. The method of claim 30, wherein an emulsion is used.

40. The method of claim 30, wherein an applicable material is used.

41. A method for spraying, dissolving, mixing, and impregnating the composition of claim 1, in paint, textile, polymers, medical devices materials, adhesives, plastics, paper, or applicable materials.

42. The method of claim 41, wherein paint is used.

43. The method of claim 41, wherein textile is used.

44. The method of claim 41, wherein polymers is used.

45. The method of claim 41, wherein a medical devices material is used.

46. The method of claim 41, wherein adhesive is used.

47. The method of claim 41, wherein plastic is used.

48. The method of claim 41, wherein paper is used.

49. A method for preparing the composition having the formula $C^{n+}X^{n-}$ in claim 1, the method comprising:
having anion biocide and cation biocide in contact with each other without using an aqueous or organic solvent solution to form the composition of $C^{n+}X^{n-}$.

* * * * *